US006054575A

United States Patent [19]
Villeponteau et al.

[11] Patent Number: 6,054,575
[45] Date of Patent: Apr. 25, 2000

[54] MAMMALIAN TELOMERASE RNA GENE PROMOTER

[75] Inventors: Bryant Villeponteau; Junli Feng, both of San Carlos; Walter Funk, Union City; William H. Andrews, Richmond, all of Calif.

[73] Assignee: Geron Corporation, Menlo Park, Calif.

[*] Notice: This patent is subject to a terminal disclaimer.

[21] Appl. No.: 08/998,443

[22] Filed: Dec. 24, 1997

Related U.S. Application Data

[63] Continuation of application No. 08/660,678, Jun. 5, 1996, Pat. No. 5,837,857, which is a continuation of application No. 08/330,123, Oct. 27, 1994, Pat. No. 5,583,016, which is a continuation-in-part of application No. 08/272,102, Jul. 7, 1994, abandoned.

[51] Int. Cl.$^7$ .................................................. C07H 21/04
[52] U.S. Cl. ......................... 536/24.31; 536/23.5; 435/6
[58] Field of Search ............................... 536/24.31; 435/6

[56] References Cited

U.S. PATENT DOCUMENTS 5,270,201  12/1993  Richards et al. ........................ 435/240

FOREIGN PATENT DOCUMENTS

| 0 666 313 A2 | 8/1995 | European Pat. Off. . | |
|---|---|---|---|
| WO 90/02757 | 3/1990 | WIPO ............................. | C07K 13/00 |

OTHER PUBLICATIONS

Mehle et al., "Telomere shortening in renal cell carcinoma," Cnacer Research, 54(1) 236–41, Jan. 1994.
Blackburn (1991), Structure and function of telomeres, Nature 350:569–573.
Blackburn (1992), Telomerases, Ann. Rev. Biochem. 61:113–129.
Blackburn et al. (1989), Recognition and elongation of telomeres by telomerase, Genome 31:553–560.
Counter et al. (1992), Telomere shortening associated with chromosome instability is arrested in immortal cells which express telomerase activity, EMBO J. 11(5) : 1921–1929.
Czech (Nov. 25, 1988), Ribozymes and their medical implications, JAMA 260(20) : 3030–3034.
Eck and Nabel (1991), Antisense oligonucleotides for therapeutic intervention, Current Opinions Biotechnology 2:897–904.
Greider (Sep. 1991), Teleomerase is processive, Mol. Cell. Bio. 11:4572–4580.
Greider and Blackburn (Dec. 24, 1987), The telomere terminal transferase of Tetrahymena is a ribonucleoprotein enzyme with two kinds of primer specificity, cell 51:887–898.
Greider and Blackburn (Jan. 26, 1989), A telomeric sequence in the RNA of Tetrahymena telomerase required for telomere repeat synthesis, Nature 337(6205):331–337.
Harley et al. (May 31, 1990), Telomeres shorten during ageing of human fibroblasts, Nature 345:458–460.

Harley et al. (1991), Telomere loss: Mitotic clock or genetic time bomb? Mut. Res. 256:271–282.
Morin (Nov. 3, 1989), The human telomere terminal transferase enzyme is a ribonucleoprotein that synthesizes TTAGGG Repeats, Cell, 59:521–529.
Morin (Oct. 8, 1991), Recognition of a chromosome truncation site associated with alpha–thalassaemia by human telomerase, Nature 353:454–456.
Romero and Blackburn (Oct. 18, 1991), A conserved secondary structure for telomerase RNA, Cell 67:343–353.
Shippen–Lentz and Blackburn (Feb. 2, 1990), Functional evidence for an RNA template in telomerase, Science 247:546–552.
Yu et al, (Mar. 8, 1990), In vitro alteration of telomere sequences and senescence caused by mutated Tetrahymena telomerase RNAs Nature 344:126–132.
Yu and Blackburn (Nov. 15, 1991), Developmentally programmed healing of chromosomes by telomerase in tetrahymena, Cell 67: 823–832.
Zahler et al. (Apr. 25, 1991), Inhibition of telomerase by G–quartet DNA structures, Nature 350:718–720.
Lingner et al. (1984), Telomerase RNAs of different ciliates have a common secondary structure and a permuted template, Gen and Development 8:1989–1998.
Singer and Gottschling (1994), TLC1: Template RNA Component of *Saccharomyces cerevislae* Telomerase, Science 266:404–409.
J. Rennie (1994) *Scientific American*, Jul. pp. 14–16, "Immortal's Enzyme".
B. Rensberger *Washington Post*, Apr. 12, 1994, pp. A1, A12, Cancer's Immortality May Depend on Enzyme.
Counter et al. (1994) PNAS 91:2900–2904. Telomerase activity in human ovarian carcinoma.
P. Nilsson et al. (1994) Oncogene 9:3043–3048, Telomerase activity in vivo in human malignant hematopoietic cells.
C.W. Greider (1993) Cold Spring Harbor Symposia on Quantitative Biology, vol. LVIII, Cold Spring Harbor Laboratory, NY. Telomerase and Telomere–length Regulation: Lessons from Small Eukaryotes to Mammals.
E.H. Blackburn (1991) *TIBS* 16:378–381 Telomeres.
Grant Abstracts: Elizabeth Blackburn—5R01 GM 32565–11; 5P30 ES01896–15UB: 9024: 5R37 GM26259–16.
Carol Greider—5R01 RG09383–03; 5R01GM43080–04.
N. Kim et al. (1994) *Science* 266:2011–2014. Specific Association of Human Telomerase Activity with Activity with Immortal Cells and Cancer.
Prowse et al. (1993) Proc. Nat. Acad. Sci., USA,90: 1493.
J. Feng et al. (1995) *Science* 269:1236–1241. The RNA Component of Human Telomerase.
Zhao et al., Cloning And Charactrization of Human and Mouse Telomerase RNA Gene Promoter Su.quence; *Oncogena* 16: 1345–1350 (1998).

*Primary Examiner*—Scott W. Houteman
*Attorney, Agent, or Firm*—Kevin R. Kaster; Amy L. Collins; Annette S. Parent

[57] ABSTRACT

Nucleic acids comprising the RNA component of a mammalian telomerase are useful as pharmaceutical, therapeutic, and diagnostic reagents.

20 Claims, No Drawings

MAMMALIAN TELOMERASE RNA GENE PROMOTER

CROSS-REFERENCE TO RELATED APPLICATIONS

This application is a continuation of and claims the benefit of U.S. patent application Ser. no. 08/660,678, filed Jun. 5, 1996, now U.S. Pat. No. 5,837,857, which is a continuation of U.S. patent application Ser. No. 08/330,123, filed Oct. 27, 1994, now U.S. Pat. No. 5,583,016, which is a continuation-in-part of U.S. patent application Ser. No. 08/272,102, filed Jul. 7, 1994, now abondened, the disclosures of which are incorporated by reference.

BACKGROUND OF THE INVENTION

1. Field of Invention

The present invention relates to human telomerase, a ribonucleoprotein enzyme involved in human telomere DNA synthesis. The invention provides methods and compositions relating to the fields of molecular biology, chemistry, pharmacology, and medical and diagnostic technology.

2. Description of Related Disclosures

The DNA at the ends or telomeres of the chromosomes of eukaryotes usually consists of tandemly repeated simple sequences. Telomerase is a ribonucleoprotein enzyme that synthesizes one strand of the telomeric DNA using as a template a sequence contained within the RNA component of the enzyme. See Blackburn, 1992, *Annu. Rev. Biochem.* 61: 113–129, incorporated herein by reference.

The RNA component of human telomerase has not been reported in the scientific literature to date, although human telomerase is known to synthesize telomeric repeat units with the sequence 5'-TTAGGG-3'. See Morin, 1989, *Cell* 59: 521–529, and Morin, 1991, *Nature* 353: 454–456, incorporated herein by reference. This knowledge has not been sufficient to enable the isolation and identification of the remainder of the nucleotide sequence of the RNA component of human telomerase. The RNA component of the telomerase enzymes of *Saccharomyces cerevisiae*, certain species of Tetrahymena, as well as that of other ciliates, such as Euplotes and Glaucoma, has been sequenced and reported in the scientific literature. See Singer and Gottschling, Oct. 21, 1994, *Science* 266: 404–409; Lingner et al., 1994, *Genes & Development* 8: 1984–1988; Greider and Blackburn, 1989, *Nature* 337: 331–337; Romero and Blackburn, 1991, *Cell* 67: 343–353; and Shippen-Lentz and Blackburn, 1990, *Science* 247: 546–552, each of which is incorporated herein by reference. The telomerase enzymes of these ciliates synthesize telomeric repeat units distinct from that in humans.

There is a great need for more information about human telomerase. Despite the seemingly simple nature of the repeat units of telomeric DNA, scientists have long known that telomeres have an important biological role in maintaining chromosome structure and function. More recently, scientists have speculated that loss of telomeric DNA may act as a trigger of cellular senescence and aging and that regulation of telomerase may have important biological implications. See Harley, 1991, *Mutation Research* 256: 271–282, incorporated herein by reference.

Methods for detecting telomerase activity, as well as for identifying compounds that regulate or affect telomerase activity, together with methods for therapy and diagnosis of cellular senescence and immortalization by controlling telomere length and telomerase activity, have also been described. See PCT patent publication No. 93/23572, published Nov. 25, 1993, and U.S. patent application Ser. Nos. 08/315,216 filed Sep. 28, 1994; 08/315,214 filed Sep. 28, 1994; 08/288,501, filed Aug. 10, 1994; 08/014,838, filed Feb. 8, 1993; 08/153,051 and 08/151,477, each filed Nov. 12, 1993; 08/060,952, filed May 13, 1993; 08/038,766, filed Mar. 24, 1993; and 07/882,438, filed May 13, 1992, each of which is incorporated herein by reference.

Significant improvements to and new opportunities for telomerase-mediated therapies and telomerase assays and screening methods could be realized if nucleic acid comprising the RNA component and/or encoding the protein components of telomerase were available in pure or isolatable form and the nucleotide sequences of such nucleic acids were known. The present invention meets these and other needs and provides such improvements and opportunities.

SUMMARY OF THE INVENTION

In a first aspect, the present invention provides the RNA component of, as well as the gene for the RNA component of, human telomerase in substantially pure form, as well as nucleic acids comprising all or at least a useful portion of the nucleotide sequence of the RNA component of human telomerase. The present invention also provides RNA component nucleic acids from other species, which nucleic acids share substantial homology with the RNA component of human telomerase, including but not limited to, the RNA components of mammals, such as primates. Other useful nucleic acids of the invention include nucleic acids with sequences complementary to the RNA component; nucleic acids. with sequences related to but distinct from nucleotide sequences of the RNA component and which interact with the RNA component or the gene for the RNA component or the protein components of human telomerase in a useful way; and nucleic acids that do not share significant sequence homology or complementarity to the RNA component or the gene for the RNA component but act on the RNA component in a desired and useful way. As described more fully below, the nucleic acids of the invention include both DNA and RNA molecules and modified analogues of either and serve a variety of useful purposes.

Thus, one type of useful nucleic acid of the invention is an antisense oligonucleotide, a triple helix-forming oligonucleotide, or other oligonucleotide that can be used in vivo or in vitro to inhibit the activity of human telomerase. Such oligonucleotides can block telomerase activity in a number of ways, including by preventing transcription of the telomerase gene (for instance, by triple helix formation) or by binding to the RNA component of telomerase in a manner that prevents a functional ribonucleoprotein telomerase from assembling or prevents the RNA component, once assembled into the telomerase enzyme complex, from serving as a template for telomeric DNA synthesis. Typically, and depending on mode of action, these oligonucleotides of the invention comprise a specific sequence of from about 10 to about 25 to 200 or more nucleotides that is either identical or complementary to a specific sequence of nucleotides in the RNA component of telomerase or the gene for the RNA component of telomerase.

Another type of useful nucleic acid of the invention is a ribozyme able to cleave specifically the RNA component of human telomerase, rendering the enzyme inactive. Yet another type of useful nucleic acid of the invention is a probe or primer that binds specifically to the RNA component of human telomerase and so can be used, e.g., to detect the presence of telomerase in a sample. Finally, useful nucleic acids of the invention include recombinant expression plasmids for producing the nucleic acids of the invention. One especially useful type of such a plasmid is a plasmid used for human gene therapy. Useful plasmids of the invention for human gene therapy come in a variety of types, including not only those that encode antisense oligonucleotides or ribozymes but also those that drive expression of the RNA component of human telomerase or a deleted or otherwise altered (mutated) version of the RNA component of human (or other species with RNA component sequences substantially homologous to the human RNA component) telomerase or the gene for the same.

In a second aspect, the invention provides methods for treating a condition associated with the telomerase activity within a cell or group of cells by contacting the cell(s) with a therapeutically effective amount of an agent that alters telomerase activity in that cell. Such agents include the telomerase RNA component-encoding nucleic acids, triple helix-froming oligonucleotides, antisense oligonucleotides, ribozymes, and plasmids for human gene therapy described above. In a related aspect, the invention provides pharmaceutical compositions comprising these therapeutic agents together with a pharmaceutically acceptable carrier or salt.

In a third aspect, the invention provides diagnostic methods for determining the level, amount, or presence of the RNA component of human telomerase, telomerase, or telomerase activity in a cell, cell population, or tissue sample, or an extract of any of the foregoing. In a related aspect, the present invention provides useful reagents for such methods (including the primers and probes noted above), optionally packaged into kit form together with instructions for using the kit to practice the diagnostic method.

In a fourth aspect, the present invention provides recombinant telomerase preparations and methods for producing such preparations. Thus, the present invention provides a recombinant human telomerase that comprises the protein components of human telomerase as well as the protein components of telomerase from a mammalian species with an RNA component substantially homologous to the RNA component of human telomerase in association with a recombinant RNA component of the invention. Such recombinant RNA component molecules of the invention include those that differ from naturally occurring RNA component molecules by one or more base substitutions, deletions, or insertions, as well as RNA component molecules identical to a naturally occurring RNA component molecule that are produced in recombinant host cells. The method for producing such recombinant telomerase molecules comprises transforming a eukaryotic host cell that expresses the protein components of telomerase with a recombinant expression vector that encodes an RNA component molecule of the invention, and culturing said host cells transformed with said vector under conditions such that the protein components and RNA component are expressed and assemble to form an active telomerase molecule capable of adding sequences (not necessarily the same sequence added by native telomerase) to telomeres of chromosomal DNA.

In a fifth aspect, the invention provides methods for purifying the protein components of human telomerase as well as the protein components of telomerase from a mammalian species with an RNA component substantially homologous to the RNA component of human telomerase. The present invention also provides methods for isolating and identifying nucleic acids encoding such protein components. In related aspects, the present invention provides purified human telomerase and purified telomerase of mammalian species with an RNA component substantially homologous to the RNA component of human telomerase, as well as purified nucleic acids that encode one or more components of such telomerase preparations. The present invention also provides pharmaceutical compositions comprising as an active ingredient the protein components of telomerase or a nucleic acid that encodes or interacts with a nucleic acid that encodes a protein component of telomerase.

Other features and advantages of the invention will be apparent from the following description of the preferred embodiments of the invention, the examples, and the claims.

DESCRIPTION OF THE PREFERRED EMBODIMENTS

The present invention provides methods, reagents, and pharmaceutical compositions relating to the ribonucleoprotein human telomerase. The invention in part arises out of the cloning and isolation of the RNA component of human telomerase and the gene for that RNA component. The nucleotide sequence of the RNA component of human telomerase is shown below. For convenience, the sequence is shown using the standard abbreviations for ribonucleotides (A is riboadenine, G is riboguanine, C is ribocytidine, and U is uridine). Those of skill in the art recognize that the sequence shown below [SEQ ID NO:1] also shows the sequence of the cDNA, in which the ribonucleotides are replaced by deoxyribonucleotides (with uridine being replaced by thymidine).

```
                                                      50
GGGUUGCGGAGGGUGGGCCUGGGAGGGGUGGUGGCCAUUUUUUGUCUAAC
                                                     100
CCUAACUGAGAAGGGCGUAGGCGCCGUGCUUUUGCUCCCCGCGCGCUGUU
                                                     150
UUUCUCGCUGACUUUCAGCGGGCGGAAAAGCCUCGGCCUGCCGCCUUCCA
                                                     200
CCGUUCAUUCUAGAGCAAACAAAAAAUGUCAGCUGCUGGCCCGUUCGCCU
                                                     250
CCCGGGGACCUGCGGCGGGUCGCCUGCCCAGCCCCCGAACCCCGCCUGGA
                                                     300
GCCGCGGUCGGCCCGGGGCUUCUCCGGAGGCACCCACUGCCACCGCGAAG
                                                     350
AGUUGGGCUCUGUCAGCCGCGGGUCUCUCGGGGGCGAGGGCGAGGUUCAC
                                                     400
CGUUUCAGGCCGCAGGAAGAGGAACGGAGCGAGUCCCGCCGCGGCGCGAU
                                                     450
UCCCUGAGCUGUGGGACGUGCACCCAGGACUCGGCUCACACAUGCAGUUC
```

```
                                                -continued
                                                                    500
GCUUUCCUGUUGGUGGGGGGAACGCCGAUCGUGCGCAUCCGUCACCCUC
                                                                    550
GCCGGCAGUGGGGGCUUGUGAACCCCCAAACCUGACUGACUGGGCCAGUG

UGCU
```

The sequence above is shown in the 5'-3' direction and is numbered for reference. The template sequence of the RNA component is believed to be located within the region defined by nucleotides 46–55 [SEQ ID NO:2], which is complementary to a telomeric sequence composed of about one-and-two-thirds telomeric repeat units.

This sequence was derived from cDNA clones and from the genomic clone of the RNA component. When the RNA component is first transcribed from the corresponding gene, at least some of the RNA transcripts produced are much longer than the ~560 nucleotide sequence shown above and in fact may comprise more than 1000 nucleotides. However, a fully functional telomerase molecule can be assembled from transcripts consisting of the ~560 nucleotide sequence shown above. The 3'-end of the RNA component in native telomerase is believed to lie within the region defined by nucleotides 514–559 in the sequence above; one analysis suggests that the 3'-end may be the U residue at nucleotide 538. Recombinant RNA component molecules comprising less than nucleotides 1–560 of the sequence shown above can also be used to prepare active telomerase.

The cloning of the RNA component of human telomerase required a novel method involving negative selection and cycles of positive selection, described below. Initially, however, an attempt was made to clone the RNA component using reverse transcription and a method for cloning the ends of cDNA called "5'-RACE" PCR amplification. The reverse transcription reaction was initiated with a primer identical to the repeat unit in the single-strand portion of human telomeric DNA and thus complementary to a sequence believed to be present in the RNA component of human telomerase. The primer also comprised, at its 5'-end, a sequence corresponding to a restriction enzyme recognition site. However, when the cDNA produced by the reverse transcription reaction and PCR amplification was examined by gel electrophoresis and nucleotide sequence analysis of the bands of nucleic acid present in the gel, only ribosomal RNA sequences were detected. Similar problems were encountered when variations of this 5'-RACE approach were attempted using nested primers.

The successful cloning effort began with the preparation of cDNA from purified preparations of human telomerase as well as from cell lines that have human telomerase activity and from cell lines that do not have detectable human telomerase activity. The method used to prepare the cDNA is described in detail in Example 1, below. Two negative selection steps and successive cycles of positive selection were used in conjunction with the cDNA preparations from the two human cell lines to lower the concentration of unwanted sequences and to raise the concentration of the desired RNA component sequences.

The negative selection steps involved the preparation of biotinylated PCR product from cDNA prepared from a human cell line that does not have detectable telomerase activity. The biotinylated PCR product was denatured and then rehybridized in a solution comprising a much lower concentration of non-biotinylated PCR product (100 biotinylated product: 1 non-biotinylated product) from cDNA prepared from a human cell line that does have telomerase activity. Given the possibility that the telomerase negative cell line might contain some low amount of the RNA component, the hybridization step was conducted to discriminate or select against only RNA expressed abundantly in both cell lines. After hybridization to a Cot selected to allow hybridization of the most abundantly expressed RNA, the unwanted material was removed by binding to streptavidinylated magnetic particles; the supernatant remaining after particle collection contained the desired cDNA for the RNA component of human telomerase. The process for PCR amplification of cDNA is described in Example 2, below.

This material was further enriched for the desired cDNA by successive cycles of positive selection. In the positive selection step, a biotinylated probe complementary to the predicted template sequence in the RNA component of human telomerase was hybridized to PCR product from an enriched (by negative selection) sample of the PCR-amplified cDNA from a human cell line that has telomerase activity. After hybridization, the probe/target complexes were bound to avidinylated magnetic beads, which were then collected and used as a source of nucleic acid enriched in RNA component sequences in further cycles of positive selection. The positive selection process is described in more detail in Examples 3 and 4, below.

After the third cycle of positive selection, the amplification products were separated by gel electrophoresis, and sections of the gel corresponding to nucleic acids ~200 bp in size were removed. The nucleic acids were then eluted from the gel sections and amplified by PCR. The PCR amplification products were digested with restriction enzyme NotI and then inserted by ligation into the NotI site of plasmid pBluescriptIISK+, commercially available from Stratagene. The resulting plasmids were transformed into E. coli host cells, and individual colonies were isolated and used as a source of nucleic acid for further analysis and DNA sequencing. Individual colonies were grown in the wells of a 96-well microtiter plate, which was then used as a master plate, and blots of DNA from the colonies in the plate were prepared and hybridized to a probe comprising a telomeric repeat sequence and therefore complementary to the RNA component of human telomerase. A number of clones positive by this test were then analyzed by DNA sequencing and a variety of other tests.

These other tests included the following: (1) determination whether antisense oligonucleotides complementary to the putative RNA component would inhibit telomerase activity in human cell extracts known to contain telomerase; (2) determination whether PCR primers specific for a putative RNA component clone sequence could be used to amplify a nucleic acid present in a telomerase sample and whether the product observed, if any, would track telomerase activity during purification of telomerase; and (3) determination whether PCR primers specific for a putative RNA component clone sequence could be used to amplify a nucleic acid present in greater abundance in cell extracts from cells in which telomerase activity is known to be high (i.e., tumor cells) than in cell extracts from cells known to produce no or only low amounts of telomerase activity. One clone, designated plasmid pGRN7, produced results in these tests consistent with the determination that the plasmid comprised cDNA corresponding to the RNA component of human telomerase.

Thus, antisense oligonucleotides corresponding to sequences of the putative RNA component sequence of pGRN7 exhibited inhibition of telomerase activity in vitro. Likewise, when telomerase was purified from cell extracts by a process involving (1) DEAE chromatography; (2) Sephadex S300 chromatography; and (3) either glycerol gradient, SP sepharose, or phenyl sepharose separation and fractions collected, PCR primers specific for the putative RNA component sequence of pGRN7 amplified a nucleic acid of the appropriate size, and the amount of amplification product correlated well with the amount of telomerase activity observed in the fractions collected. Finally, cell extracts from normal (no detectable telomerase activity) and cancer (telomerase activity present), as well as testis (telomerase activity present), cells showed corresponding amounts of PCR product upon reverse transcription and PCR amplification (RT-PCR) with primers specific for the putative RNA component comprised in pGRN7. The protocol for the RT-PCR is described in Examples 5 and 6, below.

The above results provided convincing evidence that the RNA component of human telomerase had been cloned, so plasmid pGRN7 was then used to isolate a genomic clone for the RNA component from a human cell line, as described in Example 7, below. The genomic clone was identified in and isolated from a genomic library of human DNA inserted into a lambda vector FIXII purchased from Stratagene. The desired clone comprising the RNA component gene sequences contained an ~15 kb insert and was designated clone 28-1. This clone has been deposited with the American Type Culture Collection, 10801 University Blvd., Manassas, Va 20110–2209, on Oct. 25, 1994 and is available under the accession No. 75925. Various restriction fragments were subcloned from this phage and sequenced. The gene has also been localized to the distal end of the q arm of chromosome 3. The sequence information obtained from a SauIIIA1 restriction enzyme recognition site one end of the ~15 kb insert to an internal HindIII restriction enzyme recognition site, which comprises all of mature RNA component sequence as well as transcription control elements of the RNA component gene, of lambda clone 28-1 is shown below [SEQ ID NO:3] using the standard deoxyribonucleotide abbreviations and depicted in the 5'-3' direction.

```
                                                  50
GATCAGTTAGAAAGTTACTAGTCCACATATAAAGTGCCAAGTCTTGTACT
                                                 100
CAAGATTATAAGCAATAGGAATTTAAAAAAAGAAATTATGAAAACTGACA
                                                 150
AGATTTAGTGCCTACTTAGATATGAAGGGGAAAGAAGGGTTTGAGATAAT
                                                 200
GTGGGATGCTAAGAGAATGGTGGTAGTGTTGACATATAACTCAAAGCATT
                                                 250
TAGCATCTACTCTATGTAAGGTACTGTGCTAAGTGCAATAGTGCTAAAAA
                                                 300
CAGGAGTCAGATTCTGTCCGTAAAAAACTTTACAACCTGGCAGATGCTAT
                                                 350
GAAAGAAAAAGGGGATGGGAGAGAGAGAAGGAGGGAGAGAGATGGAGAGG
                                                 400
GAGATATTTTACTTTTCTTTCAGATCGAGGACCGACAGCGACAACTCCAC
                                                 450
GGAGTTTATCTAACTGAATACGAGTAAAACTTTTAAGATCATCCTGTCAT
                                                 500
TTATATGTAAAACTGCACTATACTGGCCATTATAAAAATTCGCGGCCGGG
                                                 550
TGCGGTGGCTCATACCTGTAATCCCAGCACTTTGGGAGGCCGAAGCGGGT
                                                 600
GGATCACTTGAGCCCTGGCGTTCGAGACCAGCCTGGGCAACATGGTGAAA
                                                 650
CCCCCGTCTCTACTAAAAACACAAAAACTAGCTGGGCGTGGTGGCAGGCG
                                                 700
CCTGTAATCCCAGCTACTCAGGAGGCTGAGACACGAGAATCGCTTGAACC
                                                 750
CGGGAGCAGAGGTTGCAGTGAGCCGAGATCACGCCACTAGACTCCATCCA
                                                 800
GCCTGGGCGAAAGAGCAAGACTCCGTCTCAAAAAAAAAAATCGTTACAAT
                                                 850
TTATGGTGGATTACTCCCCTCTTTTTACCTCATCAAGACACAGCACTACT
                                                 900
TTAAAGCAAAGTCAATGATTGAAACGCCTTTCTTTCCTAATAAAAGGGAG
                                                1000
CCTCTGCTCAAGGAGAGGCTGGAGAAGGCATTCTAAGGAGAAGGGGGCAG
                                                1050
GGTAGGAACTCGGACGCATCCCACTGAGCCGAGACAAGATTCTGCTGTAG
                                                1100
TCAGTGCTGCCTGGGAATCTATTTTCACAAAGTTCTCCAAAAAATGTGAT
                                                1150
GATCAAAACTAGGAATTAGTGTTCTGTGTCTTAGGCCCTAAAATCTTCCT
                                                1200
GTGAATTCCATTTTTAAGGTAGTCGAGGTGAACCGCGTCTGGTCTGCAGA
                                                1250
GGATAGAAAAAAGGCCCTCTGATACCTCAAGTTAGTTTCACCTTTAAAGA
                                                1300
AGGTCGGAAGTAAAGACGCAAAGCCTTTCCCGGACGTGCGGAAGGGCAAC
                                                1350
```

```
                      -continued
GTCCTTCCTCATGGCCGGAAATGGAACTTTAATTTCCCGTTCCCCCCAAC
                                                  1400
CAGCCCGCCCGAGAGAGTGACTCTCACGAGAGCCGCGAGAGTCAGCTTGG
                                                  1450
CCAATCCGTGCGGTCGGCGGCCGCTCCCTTTATAAGCCGACTCGCCCGGC
                                                  1500
AGCGCACCGGGTTGCGGAGGGAGGGTGGGCCTGGGAGGGGTGGTGGCCAT
                                                  1550
TTTTTCTCTAACCCTAACTGAGAAGGGCGTAGGCGCCGTGCTTTTGCTCC
                                                  1600
CCGCGCGCTGTTTTTCTCGCTGACTTTCAGCGGGCGGAAAAGCCTCGGCC
                                                  1650
TGCCGCCTTCCACCGTTCATTCTAGAGCAAACAAAAAATGTCAGCTGCTG
                                                  1700
GCCCGTTCGCCCCTCCCGGGACCTGCGGCGGGTCGCTGCCCAGCCCCCGA
                                                  1750
ACCCCGCCTGGAGGCCGCGGTCGGCCGGGGCTTCTCCGGAGGCACCCACT
                                                  1800
GCCACCGCGAAGAGTTGGGCTCTGTCAGCCGCGGGTCTCTCGGGGCGAG
                                                  1850
GGCGAGGTTCACCGTTTCAGGCCGCAGGAAGAGGAACGGAGCGAGTCCCG
                                                  1900
CGCGCGGCGCGATTCCCTGAGCTATGGGACGTGCACCCAGGACTCGGCTC
                                                  1950
ACACATGCAGTTCGCTTTCCTGTTGGTGGGGGAACGCCGATCGTGCGCA
                                                  2000
TCCGTCACCCCTCGCCGGCAGTGGGGGCTTGTGAACCCCCAAACCTGACT
                                                  2050
GACTGGGCCAGTGTGCTGCAAATTGGCAGGAGACGTGAAGGCACCTCCAA
                                                  2100
AGTCGGCCAAAATGAATGGGCAGTGAGCCGGGGTTGCCTGGAGCCGTTCC
                                                  2150
TGCGTGGGTTCTCCCGTCTTCCGCTTTTTGTTGCCTTTTATGGTTGTATT
                                                  2200
ACAACTTAGTTCCTGCTCTGCAGATTTTGTTGAGGTTTTTGCTTCTCCCA
                                                  2250
AGGTAGATCTCGACCAGTCCCTCAACGGGGTGTGGGGAGAACAGTCATTT
                                                  2300
TTTTTTGAGAGATCATTTAACATTTAATGAATATTTAATTAGAAGATCTA
                                                  2350
AATGAACATTGGAAATTGTGTTCCTTTAATGGTCATCGGTTTATGCCAGA
                                                  2400
GGTTAGAAGTTTCTTTTTTGAAAAATTAGACCTTGGCGATGACCTTGAGC
                              2425
AGTAGGATATAACCCCCACAAGCTT
```

The RNA component sequence begins at base 1459. A variety of transcription control elements can also be identified in the sequence. An A/T Box consensus sequence is found at nucleotides 1438–1444; PSE consensus sequences are found at nucleotides 1238–1250 as well as nucleotides 1406–1414; a CAAT box consensus sequence is found at nucleotides 1399–1406; an SP1 consensus sequence is found at nucleotides 1354–1359; and a beta-interferon response element consensus sequence is found at nucleotides 1234–1245.

The plasmids described above that were constructed during the cloning of the RNA component of human telomerase and the gene for the RNA component are important aspects of the present invention. These plasmids can be used to produce the RNA component of, as well as the gene for, human telomerase in substantially pure form, yet another important aspect of the present invention. In addition, those of skill in the art recognize that a variety of other plasmids, as well as non-plasmid nucleic acids in substantially pure form, that comprise all or at least a useful portion of the nucleotide sequence of the RNA component of human telomerase are useful materials provided by the present invention.

As a general point regarding the nucleic acids and preparations containing the same of the invention, those of skill in the art recognize that the nucleic acids of the invention include both DNA and RNA molecules, as well as synthetic, non-naturally occurring analogues of the same, and heteropolymers of deoxyribonucleotides, ribonucleotides, and/or analogues of either. The particular composition of a nucleic acid or nucleic acid analogue of the invention will depend upon the purpose for which the material will be used and the environment(s) in which the material will be placed. Modified or synthetic, non-naturally occurring nucleotides, have been designed to serve a variety of purposes and to remain stable in a variety of environments, such as those in which nucleases are present, as is well known in the art. Modified or synthetic non-naturally occurring nucleotides, as compared to the naturally occurring ribo- or deoxyribonucucleotides, may differ with respect to the carbohydrate (sugar), phosphate linkage, or base portions, of the nucleotide, or may even contain a non-nucleotide base (or no base at all) in some cases. See, e.g., Arnold et al., PCT patent Publication No. WO 89/02439, entitled "Non-nucleotide Linking Reagents for Nucleotide Probes" incorporated herein by reference.

Just as the nucleic acids of the invention can comprise a wide variety of nucleotides, so too can those nucleic acids serve a wide variety of useful functions. One especially useful type of nucleic acid of the invention is an antisense oligonucleotide that can be used in vivo or in vitro to inhibit the activity of human telomerase. Antisense oligonucleotides comprise a specific sequence of from about 10 to about 25 to 200 or more (i.e., large enough to form a stable duplex but small enough, depending on the mode of delivery, to administer in vivo, if desired) nucleotides complementary to a specific sequence of nucleotides in the RNA component of human telomerase. The mechanism of action of such oligonucleotides can involve binding of the RNA component either to prevent assembly of the functional ribonucleoprotein telomerase or to prevent the RNA component from serving as a template for telomeric DNA synthesis.

Illustrative antisense oligonucleotides of the invention that serve to inhibit telomerase activity in vivo and/or in vitro include the oligonucleotides mentioned above in connection with the tests to determine whether clone pGRN7 comprised the cDNA for the RNA component of human telomerase. Three such oligonucleotides were synthesized as 2'-O-methyl RNA oligonucleotides, which bind more tightly to RNA than DNA oligonucleotides and are more resistant to hydrolysis than unmodified RNA oligonucleotides, and, as noted above, were used to demonstrate inhibition of telomerase activity in vitro. The sequence of each of these O-methyl RNA oligonucleotides is shown below.

```
T3  5'-CUCAGUUAGGGUUAGACAAA-3'   [SEQ ID NO:26]

P3  5'-CGCCCUUCUCAGUUAGGGUUAG-3'[SEQ ID NO:27]

TA3 5'-GGCGCCUACGCCCUUCUCAGUU-3'[SEQ ID NO:28[
```

These oligonucleotides can also be used to inhibit telomerase activity in human cells.

Those of skill in the art will recognize that the present invention provides a wide variety of antisense oligonucleotides able to inhibit telomerase activity. Another useful antisense oligonucleotides of the invention is oligonucleotide Tel-AU, which has the sequence 5'-CAGGCCCACCCTCCGCAACC-3' [SEQ ID NO:29] and which, like any of the antisense oligonucleotides of the invention, can be synthesized using phosphorothioate nucleotides, chiral-methyl phoshponates, naturally occurring nucleotides, or mixtures of the same to impart stability and the desired $T_m$. Those of skill in the art recognize that a wide variety of modified nucleotide analogues, such as O-methyl ribonucleotides, phosphorothioate nucleotides, and methyl phosphonate nucleotides, can be used to produce nucleic acids of the invention with more desired properties (i.e., nuclease-resistant, tighter-binding, etc.) than those produced using naturally occurring nucleotides. Other techniques for rendering oligonucleotides nuclease-resistant include those described in PCT patent publication No. 94/12633.

In addition to the antisense oligonucleotides of the invention, one can construct oligonucleotides that will bind to duplex nucleic acid either in the folded RNA component or in the gene for the RNA component, forming a triple helix-containing or triplex nucleic acid to inhibit telomerase activity. Such oligonucleotides of the invention are constructed using the base-pairing rules of triple helix formation and the nucleotide sequence of the RNA component. Such oligonucleotides can block telomerase activity in a number of ways, including by preventing transcription of the telomerase gene or by binding to a duplex region of the RNA component of telomerase in a manner that prevents the RNA component either from forming a functional ribonucleoprotein telomerase or from serving as a template for telomeric DNA synthesis. Typically, and depending on mode of action, the triplex-forming oligonucleotides of the invention comprise a specific sequence of from about 10 to about 25 to 200 or more (i.e., large enough to form a stable triple helix but small enough, depending on the mode of delivery, to administer in vivo, if desired) nucleotides "complementary" (in this context, complementary means able to form a stable triple helix) to a specific sequence in the RNA component of telomerase or the gene for the RNA component of telomerase.

In addition to the antisense and triple helix-forming oligonucleotides of the invention, "sense" oligonucleotides identical in sequence to at least a portion of the RNA component of human telomerase can also be used to inhibit telomerase activity. Oligonucleotides of the invention of this type are characterized in comprising either (1) less than the complete sequence of the RNA component needed to form a functional telomerase enzyme or (2) the complete sequence of the RNA component needed to form a functional telomerase enzyme as well as a substitution or insertion of one or more nucleotides that render the resulting RNA non-functional In both cases, inhibition of telomerase activity is observed due to the "mutant" RNA component binding the protein components of human telomerase to form an inactive telomerase molecule. The mechanism of action of such oligonucleotides thus involves the assembly of a non-functional ribonucleoprotein telomerase or the prevention of assembly of a functional ribonucleoprotein telomerase. Sense oligonucleotides of the invention of this type typically comprise a specific sequence of from about 20, 50 200, 400, 500, or more nucleotides identical to a specific sequence of nucleotides in the RNA component of human telomerase.

Thus, another useful oligonucleotide of the invention comprises an altered or mutated sequence of the RNA component of human telomerase. Yu et al., 1990, *Nature* 344: 126, shows that a mutated form of the RNA component of Tetrahymena telomerase can be incorporated into the telomerase of Tetrahymena cells and that the incorporation has deleterious effects on those cells. Incorporation of mutated forms of the RNA component of human telomerase may have similar effects on human cells that otherwise have telomerase activity without affecting normal human cells that do not have telomerase activity. Such mutated forms include those in which the sequence 5'-CTAACCCTA-3' [SEQ ID:8] is mutated to 5'-CAAACCCAA-3' [SEQ ID NO:9], 5'-CCAACCCCAA-3' [SEQ ID NO:10], or 5'-CTCACCCTCA-3' [SEQ ID NO:11]. Each of these altered RNA component sequences alters the telomeric repeat units incorporated into the chromosomal DNA, thus affecting chromosome structure and function. Such oligonucleotides can be designed to contain restriction enzyme recognition sites useful in diagnostic methods for the presence of the altered RNA component via restriction enzyme digestion of telomeric DNA or an extended telomerase substrate.

To illustrate this aspect of the invention, site-specific mutagenesis was carried out using a plasmid (designated pGRN33, available from the American Type Culture Collection, 10801 University Blvd., Manassas, VA 20110-2209, deposited Oct. 25, 1994 under accession No. ATCC 75926) that comprises an ~2.5 kb HindIII-SacI fragment from lambda clone 28-1 (see Example 7, below) as well as the SV40 origin of replication (but no promoter activity). The resulting plasmids, designated pGRN34 (comprising 5'-CAAACCCAA-3'), pGRN36 (comprising 5'-CCAACCCCAA-3'), and pGRN37 (comprising 5'-CTCACCCTCA-3'), were transformed into eukaryotic host cells (a 293-derived cell line expressing SV40 large T antigen), and telomerase assays were conducted using cell extracts from the transformants.

The assays showed that the telomerase activity in the cells resulted in the formation of nucleic acids comprising the altered sequences, indicating that the genomic clone comprised a functional RNA component gene and that the plasmids comprised an altered but functional RNA component gene. These results illustrate how the present invention provides recombinant telomerase preparations and methods for producing such preparations. The present invention provides a recombinant human telomerase that comprises the protein components of human telomerase in functional association with a recombinant RNA component of the invention. Such recombinant RNA component molecules of the invention include those that differ from naturally occurring RNA component molecules by one or more base substitutions, deletions, or insertions, as well as RNA component molecules identical to a naturally occurring RNA component molecule that are produced in recombinant host cells. The method for producing such recombinant telomerase molecules comprises transforming a eukaryotic host cell that expresses the protein components of telomerase with a recombinant expression vector that encodes an RNA component molecule of the invention, and culturing said host cells transformed with said vector under conditions such that the protein components and RNA component are expressed and assemble to form an active telomerase molecule capable of adding sequences (not necessarily the same sequence added by native telomerase) to telomeres of chromosomal DNA. Other useful embodiments of such recombinant DNA expression vectors (or plasmids) include plasmids that comprise the gene for the RNA component of human telomerase with a deletion, insertion, or other modification that renders the gene non-functional. Such plasmids are especially useful for human gene therapy to "knock-out" the endogenous RNA component gene, although a highly efficient transformation and recombination system is required, to render the treated cells irreversibly mortal.

Other oligonucleotides of the invention called "ribozymes" can also be used to inhibit telomerase activity. Unlike the antisense and other oligonucleotides described above, which bind to an RNA, a DNA, or a telomerase protein component, a ribozyme not only binds but also specifically cleaves and thereby potentially inactivates a target RNA, such as the RNA component of human telomerase. Such a ribozyme can comprise 5'- and 3'-terminal sequences complementary to the telomerase RNA. Depending on the site of cleavage, a ribozyme can render the telomerase enzyme inactive. See PCT patent publication No. 93/23572, supra. Those in the art upon review of the RNA sequence of the human telomerase RNA component will note that several useful ribozyme target sites are present and susceptible to cleavage by, for example, a hammerhead motif ribozyme. Illustrative ribozymes of the invention of this type include the ribozymes below, which are RNA molecules having the sequences indicated:

Draper et al., PCT patent publication No. 93/23569, both incorporated herein by reference. As described by Hu et al., PCT patent publication No. 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

Thus, the invention provides a wide variety of oligonucleotides to inhibit telomerase activity. Such oligonucleotides can be used in the therapeutic methods of the invention for treating disease, which methods comprise administering to a patient a therapeutically effective dose of a telomerase inhibitor or activator of the invention. One can measure telomerase inhibition or activation to determine the amount of an agent that should be delivered in a therapeutically effective dose using the assay protocols described in the copending U.S. patent applications and PCT patent publication No. 93/23572 noted above. As noted in those applications and discussed above, inhibition of telomerase activity renders an immortal cell mortal, while activation of telomerase activity can increase the replicative lifespan of a cell. Telomerase inhibition therapy is an effective treatment against cancers involving the uncontrolled growth of immortal cells, and telomerase activation is an effective treatment to prevent cell senescence. Delivery of agents that inhibit or block telomerase activity, such as an antisense oligonucleotide, a triple helix-forming oligonucleotide, a ribozyme, or a plasmid that drives expression of a mutant RNA component of telomerase can prevent telomerase action and ultimately leads to cell senescence and cell death of treated cells.

In addition, the present invention provides therapeutic methods that ensure that normal cells remain mortal; for instance, the RNA component can be modified using standard genetic engineering procedures to delete all or a portion of a natural gene encoding the component (e.g., by in vitro mutagenesis) by genetic recombination. Such cells will then be irreversibly mortal. This procedure is useful in gene therapy, where normal cells modified to contain expression plasmids are introduced into a patient, and one wants to ensure cancerous cells are not introduced or, if such cells are introduced, then those cells have been rendered irreversibly mortal.

Because telomerase is active only in tumor, germline, and certain stem cells of the hematopoietic system, other normal cells are not affected by telomerase inhibition therapy. Steps can also be taken to avoid contact of the telomerase inhibitor with germline or stem cells, although this may not be essential. For instance, because germline cells express telomerase activity, inhibition of telomerase may negatively

```
1:  5'-UAGGGUUACUGAUGAGUCCGUGAGGACGAAACAAAAAAU-3'    [SEQ ID NO:12];

2:  5'-UUAGGGUCUGAUGAGUCCGUGAGGACGAAAGACAAAA-3'     [SEQ ID NO:13];

3:  5'-UCUCAGUCUGAUGAGUCCGUGAGGACGAAAGGGUUA-3'      [SEQ ID NO:14];

and

4:  5'-CCCGAGACUGAUGAGUCCGUGAGGACGAAACCCGCG-3'      [SEQ ID NO:15].
```

Other optimum target sites for ribozyme-mediated inhibition of telomerase activity can be determined as described by Sullivan et al., PCT patent publication No. 94/02595 and impact spermatogenesis and sperm viability, suggesting that telomerase inhibitors may be effective contraceptives or sterilization agents. This contraceptive effect may not be desired, however, by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient.

Other therapeutic methods of the invention employ the telomerase RNA nucleic acid of the invention to stimulate telomerase activity and to extend replicative cell life span. These methods can be carried out by delivering to a cell a functional recombinant telomerase ribonucleoprotein of the invention to the cell. For instance, the ribonucleoprotein can be delivered to a cell in a liposome, or the gene for the RNA component of human telomerase (or a recombinant gene with different regulatory elements) can be used in a eukaryotic expression plasmid (with or without sequences coding for the expression of the protein components of telomerase) to activate telomerase activity in various normal human cells that otherwise lack detectable telomerase activity due to low levels of expression of the RNA component or a protein component of telomerase. If the telomerase RNA component is not sufficient to stimulate telomerase activity, then the RNA component can be transfected along with genes expressing the protein components of telomerase to stimulate telomerase activity. Thus, the invention provides methods for treating a condition associated with the telomerase activity within a cell or group of cells by contacting the cell(s) with a therapeutically effective amount of an agent that alters telomerase activity in that cell.

Cells that incorporate extra copies of the telomerase RNA gene can exhibit an increase in telomerase activity and an associated extended replicative life span. Such therapy can be carried out ex vivo on cells for subsequent introduction into a host or can be carried out in vivo. The advantages of stabilizing or increasing telomere length by adding exogenous telomerase genes ex vivo to normal diploid cells include: telomere stabilization can arrest cellular senescence and allow potentially unlimited amplification of the cells; and normal diploid cells with an extended life span can be cultured in vitro for drug testing, virus manufacture, or other useful purposes. Moreover, ex vivo amplified stem cells of various types can be used in cell therapy for particular diseases, as noted above.

Telomere stabilization can also suppress cancer incidence in replicating cells by preventing telomeres from becoming critically short as cells near crisis. During crisis, massive genomic instability is generated as the protective effect of the telomeric cap is lost. The "genetic deck" is reshuffled, and almost all cells die. The rare cells that emerge from this process are typically aneuploid with many gene rearrangements and end up reestablishing stability in their telomeres by expressing telomerase. If crisis can be prevented by keeping telomeres long, then the genomic instability associated with crisis can also be prevented, limiting the chances that an individual cell will suffer the required number of genetic mutations needed to spawn a metastatic cancer.

Cells that can be targeted for telomerase gene therapy (therapy involving increasing the telomerase activity of a target cell) include but are not limited to hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

Typically, the therapeutic methods of the invention involve the administration of an oligonucleotide that functions to inhibit or stimulate telomerase activity under in vivo physiological conditions and will be stable under those conditions. As noted above, modified nucleic acids may be useful in imparting such stability, as well as for ensuring delivery of the oligonucleotide to the desired tissue, organ, or cell. Methods useful for delivery of oligonucleotides for therapeutic purposes are described in Inouye et al., U.S. Pat. No. 5,272,065, incorporated herein by reference.

While oligonucleotides can be delivered directly as a drug in a suitable pharmaceutical formulation, one can also deliver oligonucleotides using gene therapy and recombinant DNA expression plasmids of the invention. One such illustrative plasmid is described in Example 8, below. In general, such plasmids will comprise a promoter and, optionally, an enhancer (separate from any contained within the promoter sequences) that serve to drive transcription of an oligoribonucleotide, as well as other regulatory elements that provide for episomal maintenance or chromosomal integration and for high-level transcription, if desired. Adenovirus-based vectors are often used for gene therapy and are suitable for use in conjunction with the reagents and methods of the present invention. See PCT patent publication Nos. 94/12650; 94/12649; and 94/12629. Useful promoters for such purposes include the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), and the constitutive CMV promoter. A plasmid useful for gene therapy can comprise other functional elements, such as selectable markers, identification regions, and other genes. Recombinant DNA expression plasmids can also be used to prepare the oligonucleotides of the invention for delivery by means other than by gene therapy, although it may be more economical to make short oligonucleotides by in vitro chemical synthesis.

In related aspects, the invention features pharmaceutical compositions including a therapeutically effective amount of a telomerase inhibitor or telomerase activator of the invention. Pharmaceutical compositions of telomerase inhibitors of the invention include a mutant RNA component of human telomerase, an antisense oligonucleotide or triple helix-forming oligonucleotide that binds the RNA component or the gene for the same of human telomerase, or a ribozyme able to cleave the RNA component of human telomerase, or combinations of the same or other pharmaceuticals in a pharmaceutically acceptable carrier or salt. Other pharmaceutical compositions of the invention comprise a telomerase activator preparation, such as purified human telomerase or mRNA for the protein components of telomerase and the RNA component of telomerase, and are used to treat senescence-related disease. The therapeutic agent can be provided in a formulation suitable for parenteral, nasal, oral, or other mode of administration. See PCT patent publication No. 93/23572, supra.

The present invention provides diagnostic methods and reagents in addition to the pharmaceutical formulations and therapeutic methods described above. The invention provides diagnostic methods for determining the level, amount, or presence of the RNA component of human telomerase, telomerase, or telomerase activity in a cell, cell population, or tissue sample. In a related aspect, the present invention provides useful reagents for such methods, optionally packaged into kit form together with instructions for using the kit to practice the diagnostic method. As noted above in connection with the tests conducted to determine that clone pGRN7 contained the cDNA for the RNA component of human telomerase, the levels of the RNA component are elevated in tumor cells. Thus, detection of the RNA component is a useful diagnostic for tumor cells.

In addition, probes or primers that bind specifically to the RNA component of human telomerase (or either strand of the gene for the same) can be used in diagnostic methods to detect the presence of telomerase nucleic acid in a sample. Primers and probes are oligonucleotides that are complementary, and so will bind, to a target nucleic acid. Although primers and probes can differ in sequence and length, the primary differentiating factor is one of function: primers serve to initiate DNA synthesis, as in PrR amplification, while probes are typically used only to bind to a target nucleic acid. Typical lengths for a primer or probe can range from 8 to 20 to 30 or more nucleotides. A primer or probe can also be labeled to facilitate detection (i.e., radioactive or fluorescent molecules are typically used for this purpose) or purification/separation (i.e., biotin or avidin is often used for this purpose).

An especially preferred diagnostic method of the invention involves the detection of telomerase RNA component sequences in cell or tissue samples taken from patients suspected to be at risk for cancer. Such methods will typically involve binding a labelled probe or primer to an RNA component sequence under conditions such that only perfectly matched (complementary) sequences bind (hybridize) to one another. Detection of labelled material bound to RNA in the sample will correlate with the presence of telomerase activity and the presence of cancer cells. Some cells may express the RNA component of telomerase but remain telomerase-negative due to lack of expression of the protein components of telomerase. If one desired to detect the presence of telomerase activity in such cells, then one could first isolate protein and then determine whether the protein fraction contains the telomerase RNA component, which would signal the presence of telomerase activity. The diagnostic methods of the invention may be especially useful in detecting the presence of telomerase activity in tissue biopsies and histological sections in which the method is carried out in situ, typically after amplification of telomerase RNA component using specific PCR primers of the invention.

Depending on the length and intended function of the primer, probe, or other nucleic acid comprising sequences from the RNA component of human telomerase, expression plasmids of the invention may be useful. For instance, recombinant production of the full-length RNA component of the invention can be carried out using a recombinant DNA expression plasmid of the invention that comprises a nucleic acid comprising the nucleotide sequence of the RNA component positioned for transcription under the control of a suitable promoter. Host cells for such plasmids can be either prokaryotic or eukaryotic, and the promoter, as well as the other regulatory elements and selectable markers chosen for incorporation into the expression plasmid will depend upon the host cell used for production.

The intact RNA component gene, i.e., the promoter, which includes any regulatory sequences in the 5'-region of the gene, and RNA component coding region, can be used to express the RNA component in human cells, including human cells that have been immortalized by viral transformation or cancer. The promoter of the RNA component gene may be regulated, however, and for this and other reasons, one may want to express the RNA component under the control of a different promoter. On the other hand, the promoter of the RNA component gene can be used independently of the RNA component coding sequence to express other coding sequences of interest. For instance, one could study the transcriptional regulation of the RNA component gene by fusing the promoter of the RNA component gene to a coding sequence for a "reporter" coding sequence, such as the coding sequence for beta-galactosidase or another enzyme or protein the expression of which can be readily monitored. Thus, the promoter and other regulatory elements of the gene for the RNA component of human telomerase can be used not only to express the RNA component but also protein components of human telomerase, antisense or other oligonucleotides, as well as other gene products of interest in human cells. Expression plasmids comprising the intact gene for the RNA component of human telomerase can be especially useful for a variety of purposes, including gene therapy. Those of skill in the art recognize that a wide variety of expression plasmids can be used to produce useful nucleic acids of the invention and that the term "plasmid", as used herein, refers to any type of nucleic acid (from a phage, virus, chromosome, etc.) that can be used to carry specific genetic information into a host cell and maintain that information for a period of time.

As indicated by the foregoing description, access to purified nucleic acids comprising the sequence of the RNA component of human telomerase provides valuable diagnostic and therapeutic methods and reagents, as well as other important benefits. One important benefit of the present invention is that the methods and reagents of the invention can be used to isolate the RNA component and genes for the RNA component of telomerase from any mammalian species that has an RNA component substantially homologous to the human RNA component of the present invention. The phrase "substantially homologous" refers to that degree of homology required for specific hybridization of an oligonucleotide or nucleic acid sequence of the human RNA component to a nucleic acid sequence of an RNA component sequence of another mammalian species. Given such substantial homology, those of ordinary skill in the art can use the nucleic acids and oligonucleotide primers and probes of the invention to identify and isolate substantially homologous sequences.

For instance, one can probe a genomic or cDNA library to detect homologous sequences. One can also use primers corresponding to regions of the RNA component sequence and PCR amplification under low or moderate stringency conditions to amplify a specific homologous nucleic acid sequence from preparations of RNA or DNA from a mammalian species. By using these and other similar techniques, those of ordinary skill can readily isolate not only variant RNA component nucleic acids from human cells but also homologous RNA component nucleic acids from other mammalian cells, such as cells from primates, from mammals of veterinary interest, i.e., cattle, sheep, horse, dogs, and cats, and from rodents, i.e., rats, mice, and hamsters. In turn, these nucleic acids can be used to prepare transgenic animals of great value for screening and testing of pharmaceuticals that regulate telomerase activity. For instance, by using a plasmid of the invention, one can "knock out" the RNA component gene or replace the natural RNA component gene with a recombinant inducible gene in a mus spretus embryonic stem cell and then generate a transgenic mouse that will be useful as a model or test system for the study of age- or senescence-related disease. Example 9, below, illustrates how such methodology has been used to identify and isolate RNA component sequences of primates.

The reagents of the present invention also allow the cloning and isolation of nucleic acids encoding the protein components of human as well as other mammalian telomerase enzymes, which have not previously been available. Access to such nucleic acids provide complementary benefits to those provided by the nucleic acids comprising nucleic acid sequences of the RNA component of human telomerase. For instance, and as noted above, the therapeutic benefits of the present invention can be enhanced, in some instances, by use of purified preparations of the protein components of human telomerase and by access to nucleic acids encoding the same. The nucleic acids of the invention that encode the RNA component of human telomerase can be used to isolate the nucleic acid encoding the protein components of human telomerase, allowing access to such benefits. Thus, the invention provides methods for isolating and purifying the protein components of human telomerase, as well as for identifying and isolating nucleic acids encoding the protein components of human telomerase. In related aspects, the present invention provides purified human telomerase, purified nucleic acids that encode the protein components of human telomerase, recombinant expression plasmids for the protein components of human telomerase. The invention also provides pharmaceutical compositions comprising as an active ingredient either the protein components of human telomerase or a nucleic acid that either encodes those protein components or interacts with nucleic acids that encode those protein components, such as antisense oligonucleotides, triple helix-froming oligonucleotides, ribozymes, or recombinant DNA expression plasmids for any of the foregoing.

The cloned RNA component of human telomerase can be used to identify and clone nucleic acids encoding the protein components of the ribonucleoprotein telomerase enzyme.

Several different methods can be employed to achieve identification and cloning of the protein components. For instance, one can use affinity capture of the enzyme or partially denatured enzyme using as an affinity ligand either (1) nucleotide sequences complementary to the RNA component to bind to the RNA component of the intact enzyme; or (2) the RNA component to bind the protein components of a partially or fully denatured enzyme. The ligand can be affixed to a solid support or chemically modified (e.g., biotinylated) for subsequent immobilization on the support. Exposure of cell extracts containing human telomerase, followed by washing and elution of the telomerase enzyme bound to the support, provides a highly purified preparation of the telomerase enzyme. The protein components can then be optionally purified further or directly analyzed by protein sequencing. The protein sequence determined can be used to prepare primers and probes for cloning the cDNA or identifying a clone in a genomic bank comprising nucleic acids that encode a protein component of telomerase.

Affinity capture of telomerase utilizing an engineered RNA component can also be conducted using in vitro transcribed telomerase RNA and a system for the reconstitution of telomerase enzyme activity. See Autexier and Greider, 1994, *Genes & Development* 8: 563–575, incorporated herein by reference. The RNA is engineered to contain a tag, similar to epitope tagging of proteins. The tag can be an RNA sequence to which a tightly binding ligand is available, e.g., an RNA sequence-specific antibody, a sequence-specific nucleic acid binding protein, or an organic dye that binds tightly to a specific RNA sequence. The tolerance of telomerase for the tag sequence and position can be tested using standard methods. Synthesis of the altered RNA component and the reconstitution step of this method can also be carried out in vivo. Affinity capture using the immobilized ligand for the RNA tag can then be used to isolate the enzyme.

Expression screening can also be used to isolate the protein components of the telomerase enzyme. In this method, cDNA expression libraries can be screened with labeled telomerase RNA, and cDNAs encoding proteins that bind specifically to telomerase RNA can be identified. A molecular genetic approach using translational inhibition can also be used to isolate nucleic acids encoding the protein components of the telomerase enzyme. In this method, telomerase RNA sequences will be fused upstream of a selectable marker. When expressed in a suitable system, the selectable marker will be functional. When cDNA encoding a telomerase RNA binding protein is expressed, the protein will bind to its recognition sequence thereby blocking translation of the selectable marker, thus allowing for identification of the clone encoding the protein. In other embodiments of this method, the blocked translation of the selectable marker will allow transformed cells to grow. Other systems that can be employed include the "interaction trap system" described in PCT patent publication No. WO 94/10300; the "one-hybrid" system described in Li and Herskowitz, Dec. 17, 1993, *Science* 262: 1870–1874, and Zervos et al., Jan. 29, 1993, *Cell* 72: 223–232; and the "two-hybrid" system commercially available from Clontech.

Telomerase RNA binding or telomerase activity assays for detection of specific binding proteins and activity can be used to facilitate the purification of the telomerase enzyme and the identification of nucleic acids that encode the protein components of the enzyme. For example, nucleic acids comprising RNA component sequences can be used as affinity reagents to isolate, identify, and purify peptides, proteins or other compounds that bind specifically to a sequence contained within the RNA component, such as the protein components of human telomerase. Several different formats are available, including gel shift, filter binding, footprinting, Northwestern (RNA probe of protein blot), and photocrosslinking, to detect such binding and isolate the components that bind specifically to the RNA component. These assays can be used to identify binding proteins, to track purification of binding proteins, to characterize the RNA binding sites, to determine the molecular size of binding proteins, to label proteins for preparative isolation, and for subsequent immunization of animals for antibody generation to obtain antibodies for use in isolating the protein or identifying a nucleic acid encoding the protein in a coupled transcription/translation system.

As will be apparent to those of skill in the art upon reading of this disclosure, the present invention provides valuable reagents relating to human telomerase, as well as a variety of useful therapeutic and diagnostic methods. The above description of necessity provides a limited sample of such methods, which should not be construed as limiting the scope of the invention. Other features and advantages of the invention will be apparent from the following examples and claims.

The following examples describe specific aspects of the invention to illustrate the invention and provide a description of the methods used to isolate and identify the RNA component of human telomerase for those of skill in the art. The examples should not be construed as limiting the invention, as the examples merely provide specific methodology useful in understanding and practice of the invention.

EXAMPLE 1

Preparation of PCR-amplifiable cDNA

RNA was obtained from 293 cells by guanidine-thiocyanate extraction or from purified telomerase fractions by phenol/chloroform extractions. The total RNA from 293 cells was size fractionated on a 2% agarose gel, and the RNA below 500 bp was isolated.

First strand cDNA synthesis was performed with Superscript™ II reverse transcriptase obtained from Bethesda Research Laboratories (BRL). About 0.5 to 1.0 μg RNA was mixed with about 40 ng of random primer (6 mer) in water at a total volume of 11 μl. The solution was heated for 10 min. at 95° C. and then cooled on ice for 5–10 min. The denatured nucleic acid was collected by centrifugation. The denatured RNA and primer mixture were then resuspended by adding, in the order shown: 4 μl 5×1st strand synthesis buffer; 2 μl 0.1 M dithiothreitol (DTT); 1 μl RNAsin (Pharmacia); and 1 μl dNTP (0.125 mM each for 0.5 mM total concentration). The reaction mixture was incubated at 42° C. for 1 min., and then, 1 μl (200 units) of Superscript™ II RTase (BRL) was added and mixed into the reaction, which was then incubated for 60 min. at 42° C. The resulting reaction mixture, containing the newly synthesized cDNA was placed on ice until second strand synthesis was performed.

Second strand cDNA synthesis was performed as follows. About 20 μl of the reaction mixture from the first strand cDNA synthesis reaction mixture (from above) was mixed with, in the order shown, the following components: 111.1 μl of water; 16 μl of 10× *E. coli* DNA ligase buffer; 3 μl of dNTP (2.5 mM each stock); 1.5 μl of *E. coli* DNA ligase (15 units from BRL); 7.7 μl of *E. coli* DNA polymerase (40 units from Pharmacia); and 0.7 μl of *E. coli* RNase H (BRL). The resulting solution was gently mixed and incubated for 2 hours at 16° C., at which time 1 μl (10 units) of T4 DNA polymerase was added to the reaction tube and incubation continued for 5 min. at the same temperature (16° C.). The reaction was stopped, and the nucleic acid was collected by extracting the reaction with phenol/chloroform twice, precipitating the nucleic acid with ethanol, and centrifuging the reaction mixture to pellet the nucleic acid.

The cDNA pellet collected by centrifugation was resuspended in 20 μl of TE buffer and ligated to a double-stranded oligonucleotide called "NotAB" composed of two oligonucleotides (NH2 is an amino blocking group):

```
NotA: 5'-pATAGCGGCCGCAAGAATTCA-NH2   [SEQ ID NO:16]

NotB: 5'-TGAATTCTTGCGGCCGCTAT-3'    [SEQ ID NO:17]
```

The double-stranded oligonucleotide was made by mixing 50 μl of NotA oligonucleotide (100 pmol) with 50 μl of NotB oligonucleotide (100 pmol) in 46.25 μl of water, heating the resulting solution for 5 min. at 95° C., and adding 3.75 μl of 20× SSC buffer while the solution was still hot. The tube containing the mixture was then placed in a beaker containing hot water (at a temperature of about 70 to 75° C.), the temperature of which was allowed to drop slowly to below 15° C., so that the two oligonucleotides could hybridize to form the double-stranded oligonucleotide NotAB. The resulting nucleic acid was collected by precipitation and centrifugation.

The double-stranded NotAB oligonucleotide was resuspended in about 30 μl TE buffer and then ligated to the cDNA in a reaction mixture containing 10 μl of the cDNA preparation described above, about 50 pmol (calculated by OD260) of NotAB; 2 μl of 10× T4 DNA ligase buffer; 1.2 μl of T4 DNA ligase; 0.2 μl of 10 mM ATP; and water in a total volume of 20 μl by incubating the reaction mixture at 16° C. overnight. The reaction was then heat-inactivated by heating the reaction mixture for 10 min. at 65° C. About 1 to 2 μl of the resulting mixture was typically used for PCR amplification; one can amplify the ligation mixture for 10 to 15 cycles (94° C., 45 seconds; 60° C., 45 seconds; and 72° C., 1.5 min.) and save as a stock, as described in Example 2.

EXAMPLE 2

PCR Amplification of cDNA

The cDNA was routinely amplified by preparing an amplification reaction mixture composed of 5 μl of 10× PCR buffer (500 mM KCl; 100 mM Tris, pH=8.3; and 20 mM MgCl$_2$; 5–8 μl of dNTP (2.5 mM each); 1 μl of Taq polymerase (Boehringer-Mannheim); 0.1 μl of gene 32 protein (Boehringer-Mannheim); 6 μl of NotB primer (20 μM stock); 2 μl of the cDNA (prepared as described in Example 1), and water to 50 μl. This mixture was then overlayed with 50 to 100 μl of mineral oil, and PCR amplification was performed for 10 to 15 cycles of 94° C., 45 seconds; 60° C., 45 seconds; and 72° C., 1.5 min. After amplification, the reaction mixture was extracted with phenol/chloroform, and the amplified nucleic acid was precipitated with ethanol and collected by centrifugation. The precipitate was then dissolved in 100 μl of TE buffer to prepare a stock solution.

EXAMPLE 3

PCR Amplification for Cyclic Selection

To make PCR product for cyclic selection, about 1 μl of a stock solution prepared as described in Example 2 was amplified in 50 μl of PCR reaction mixture prepared as described in Example 2, except that 21–24 cycles of primer annealing, extension, and denaturation of product were conducted. After amplification, reaction mixtures were extracted with phenol/chloroform, precipitated with ethanol, and collected by centrifugation. Product yield was estimated by staining with ethidium bromide after agarose gel electrophoresis of a small aliquot of the reaction mixture. Typically, about 2 μg of the nucleic acid product were used for cyclic selection.

After cyclic selection, described in Example 4, about 1 to 2 μl of the selected "pull-down" products (out of a total volume of 20 μl) were PCR amplified as described in Example 2 for 22 cycles, precipitated with ethanol, and collected by centrifugation in preparation for further cyclic selection.

EXAMPLE 4

Positive Selection of PCR-amplified cDNA

For the positive selection step of the cyclic selection process used to clone the RNA component of human telomerase, about 2 μg of the PCR-amplified cDNA were diluted into 25 μl of TE buffer and then mixed with 1.25 μl of 20× SSC and the resulting solution heated to 95° C. for 3 min. The temperature was lowered to 60° C. for 5 min., and one μl (0.1 μg/μl) of the R2 or R4 biotinylated probe was added. The sequences of these probes are shown below. The probes are O-methyl-RNA probes, so U is O-methyl-uridine, A is O-methyl-riboadenine, G is O-methyl-riboguanine, and I is inosine.

```
R2:  5'-UUAGGGUUAGII-biotin       [SEQ ID NO:18]

R4:  5'-AUUGGGUUAUII-biotin       [SEQ ID NO:19]
```

The R2 probe is specific for the telomere repeat, and the R4 probe is specific for RNase P, which was used to track the effectiveness and efficiency of the cyclic selection process. By carrying out a cyclic selection simultaneously but separately for RNase P RNA, a molecule of known sequence, one can have greater confidence that the cyclic selection process is functioning properly with respect to the molecule of interest, in this case the RNA component of human telomerase.

After either the R2 or R4 probe was added to the mixture at 65° C., the temperature of the hybridization reaction mixture was lowered to 30° C. by incubating the mixture at that temperature for 5 min., and then the reaction mixtures were further lowered to a temperature of 14° C. by incubating at that temperature for 60 min. Finally, the mixture was incubated at 4° C. for 2–12 hours.

The entire hybridization reaction mixture for each sample (R2 or R4) was added to 400 µl of 0.5× SSC at 4° C. and then added to a tube of ice-cold magnetic beads, which were purchased from Promega and pre-washed four times with 0.5× SSC before use. The resulting mixture was incubated 30 min. at 4° C. to ensure complete binding to the magnetic beads. Each reaction tube was then incubated briefly at room temperature on the magnetic stand (Promega) to pull down the beads. The beads were resuspended in cold 0.5× SSC (600 µl) and placed (in a tube) on ice. The samples were washed three more times with 0.5× SSC in this manner. Nucleic acid was eluted from the beads by resuspending the beads in 100 µl of water and incubating for 2 min. at 65° C. before placing the beads back on the magnetic stand for collection. This process was repeated three more times; the last time, the resuspended beads were incubated for 5 min. at 65° C. before placing the beads on the magnetic stand for collection. All of the 100 µl supernatants (for each sample) were pooled and dried down to 20 µl in a SpeedVac™ centrifuge. The recovered DNA was then PCR amplified for another round of amplification and selection. After each amplification, the PCR products were phenol-chloroform extracted twice, ethanol precipitated, and resuspended in 20 µl of TE buffer.

Typically, PCR amplifications were verified by agarose gel electrophoresis. In addition, a variety of controls were used to monitor the cyclic selection process. As one control, PCR "arms" (oligonucleotides of defined sequence that serve as primer hybridization sites) were placed on a nucleic acid that comprised a neomycin resistance-conferring gene. The resulting nucleic acid was mixed with the PCR-amplified cDNA and monitored at each selection by quantitative PCR. As another control, RNase P was followed in both the RNase P selected and the telomerase RNA component selected libraries.

EXAMPLE 5

RT-PCR Protocol

The first strand cDNA was made in substantial accordance with the procedure described in Example 1. Basically, RNA was purified from each telomerase fraction containing 0.1 to 1 µg RNA; typical, about one-third to one-fifth of the RNA made from a 300 µl fraction was used. The RNA was mixed with 40 to 80 ng random hexamer in 10 µl, denatured for 10 min. at 95° C. (using a thermal-cycling instrument), and chilled on ice. The denatured RNA and 6-mer were added to a reaction mixture containing 4 µl of 5× 1st strand synthesis buffer supplied by the manufacturer of the reverse transcriptase (RTase, purchased from BRL), 2 µl of 0.1 M DTT, 1 µl of 10 mM dNTP (each), 1 µl of RNase inhibitor (Pharmacia), and water to a total volume of 9 µl. The combined mixture was placed into a 42° C. water bath. After 1–2 min. incubation, 1 µl of Superscript™ II RTase (BRL) was added to the mixture. The incubation was continued for 60 min. at 42° C. The reaction was stopped by heating the tube for 10 min. at 95–98° C. The first strand cDNA was collected by brief centrifugation, aliquoted to new tubes, quickly frozen on dry ice, and stored at −80° C. or used immediately.

EXAMPLE 6

PCR Amplification of cDNA with a Specific Primer Set

For a 20 µl PCR reaction with radioactively labeled nucleotides, 1 µl of the cDNA prepared in accordance with the procedure of Example 5 was mixed with 20 pmol of primer 1, 20 pmol of primer 2, 2.5 µl of 2.5 mM dNTP, 5 µCi of alpha-$^{32}$P-dATP, 2 units of Taq polymerase (Boehringer-Mannheim), 0.2 µg of T4 gene 32 protein (Boehringer-Mannheim), 2 µl of 10× buffer (500 mM KCl, 100 mM Tris-HCl-pH8.3, and 20 mM MgCl$_2$), and water to a total volume of 20 µl. One drop of mineral oil was then added to the tube.

The PCR amplification conditions for the telomerase RNA component clone were: 94° C. for 45 sec., 60° C. for 45 sec., 72° C. for 1.5 min. The number of cycles differed depending on the type of purified materials used for RNA preparation but typically range from 18 to 25 cycles. As for all quantitative RT-PCR, several reactions with differing cycles were run for each sample to determine when the PCR amplification became saturated and non-linear.

For the RNase P used as a control, the PCR amplification conditions were: 94° C. for 45 sec., 50° C. for 45 sec., and 72° C. for 1.5 min. Again, the number of cycles ranged from 15 to 22 cycles, depending on the nature of the samples. The sequences of the primers used for RNase P amplification are shown below:

```
P3:  5'-GGAAGGTCTGAGACTAG-3'      [SEQ ID NO:20]

P4:  5'-ATCTCCTGCCCAGTCTG-3'      [SEQ ID NO:21]
```

The PCR product obtained with these two primers is about 110 bp in size.

After PCR, the products (5 to 10 µl of the reaction mixture) were loaded onto a 6% native polyacrylamide gel and electrophoresed. After electrophoresis, the gel was dried and exposed to a PhosphorImager™ cassette or to autoradiographic film for analysis.

EXAMPLE 7

Cloning the Gene for the RNA Component of Human Telomerase

The procedures used to clone the gene for the RNA component of human telomerase were carried out as generally described in Maniatis et al., *Laboratory Molecular Cloning Manual*. A genomic DNA library of DNA from the human lung fibroblast cell line WI-38 inserted into phage lambda vector FIXII was purchased from Stratagene. The phage were plated at a concentration of about 25,000 plaques per plate onto three sets of 15 (150 mm) plates. The plates were made with NZY agar and NZY top agarose; the cells used for the phage transformation were XL1BlueM-RAP2 cells; and the transformants were grown overnight for about 16 hours at 37° C. The plates were then chilled at 4° C. for about an hour, and then the plaques were "lifted" onto C/P nylon circles (filter paper from Bio Rad). This process was repeated to produce a duplicate set of lifted filters. The filters (in duplicate) were denatured, neutralized, equilibrated in 6× SSC buffer, exposed to UV irradiation to cross-link the nucleic acid to the filter, and then dried on blotter paper.

Prehybridization was conducted for one hour at 37° C. in 50% formamide buffer. The filters were probed with an ~218 bp, radioactively-labeled, NotI fragment from clone pGRN7, which had been isolated by electroelution from a 5% polyacrylamide gel after separation by electrophoresis and then nick-translated with alpha-$^{32}$P-dCTP using a nick-translation kit from Boehringer-Mannheim Biochemicals in accordance with the manufacturer's instructions. About 25 ng (~10 μCi label) of the probe were used per filter, and hybridization was conducted overnight at 37° C. in 50% formamide hybridization buffer. After hybridization, the filters were washed at room temperature six times; the first three washes were with 6× SSC containing 0.1% SDS, and the last three washes were with 6× SSC alone. After an initial exposure of several duplicate filters in a PhosphorImager™ cassette to check hybridization efficiency and signal strength, the filters were washed at 65° C. in 0.5× SSC. The filters were then placed under Kodak XAR5 film using two intensifier screens and allowed to expose the film for about 100 hours at −70° C.

One strong signal emanated from the filter containing a phage, later designated 28-1, comprising the gene for the RNA component of human telomerase. The plaque corresponding to the signal observed on the filter was used to make secondary plates, so that an isolated plaque (confirmed by probing with labeled pGRN7 nucleic acid) could be cultured for large-scale isolation of the phage DNA. Phage 28-1, available from the American Type Culture Collection, 10801 University Blvd., Manassas, VA 20110-2209, on Oct. 25, 1994 under accession No. 75925 comprises an ~15 kb insert and comprises several restriction fragments that contain sequences that hybridize with RNA component sequences on pGRN7: a 4.2 kb EcoRI restriction enzyme fragment; a 4.2 kb ClaI restriction enzyme fragment, and a 2.5 kb HindIII-SacI restriction enzyme fragment. The latter fragment comprises the entire ~560 nucleotide sequence of the RNA component shown above and is believed to comprise the complete gene for the RNA component. The plasmid comprising the 2.5 kb HindIII-SacI restriction enzyme fragment in the pBluescript vector was designated plasmid pGRN33 and is available from the American Type Culture Collection, 10801 University Blvd., Manassas, VA 20110-2209, on Oct. 25, 1994 under the accession No. ATCC 75926. To the extent the human gene may comprise sequences other than those on the 2.5 kb fragment, those sequences can be isolated from phage 28-1 or from other phage clones identified by probing with the 2.5 kb fragment (or another probe of the invention).

The restriction enzyme fragments noted above were prepared in separate restriction enzyme digests; the products of the digests were separated by electrophoresis on a 0.7% agarose gel or, for the ~2.5 kb fragment only, a 3% poly-acrylamide gel; and the desired bands were cut from the gel and prepared for subcloning either by using the GeneClean™ Kit II (from Bio101, Inc.) or by electroelution into Spectropor #2 dialysis tubing in 0.1× TBE at 100 V for two hours (for the ~2.5 kb fragment only).

These restriction enzyme fragments were subcloned into E. coli expression/mutagenesis plasmids derived from pUC-based plasmids or from pBluescriptII plasmids that also comprise an SV40 origin of replication (but no SV40 promoter activity). The resulting plasmids can be used to prepare altered (mutated) RNA component nucleic acids for introduction into human or other eukaryotic cells for a variety of purposes, as described above in the Description of the Preferred Embodiments.

EXAMPLE 8

Antisense Plasmids for the RNA Component of Human Telomerase

Antisense expression plasmids were prepared by PCR amplification of RNA component cDNA using the following primer sets: (1) NotB and G1, which produces an antisense nucleic acid that is smaller than the cDNA insert in the plasmid; and (2) NotB and R3C, which produces a full-length (relative to the insert in the plasmid) antisense nucleic acid. The nucleotide sequence of NotB is shown in Example 1, above; the nucleotide sequences of the G1 and R3C primers are shown below.

```
                                           [SEQ ID NO:22]
G1:  5'-GAGAAAAACAGCGCGCGGGGAGCAAAAGCA-3'

[SEQ ID NO:23]
R3C: 5'-GTTTGCTCTAGAATGAACGGTGGAAG-3'
```

After PCR amplification, the amplified fragments were cloned into an ~10 kb expression plasmid at a PmlI site; the plasmid comprises puromycin resistance-conferring, DHFR, and hygromycin B resistance-conferring genes as selectable markers, the SV40 origin of replication; the inducible human metallothionein gene promoter positioned for expression of the antisense strand of the gene for the RNA component of human telomerase (one could also use a stronger promoter to get higher expression levels), and the SV40 late poly A addition site.

The resulting plasmids (designated pGRN42 for the NotB/G1 product and pGRN45 for the NotB/R3C product) were transfected by the calcium phosphate procedure (see Maniatis et al., supra) into the fibrosarcoma cell line HT1080. HT1080 cells are normally immortal; expression of the antisense RNA for the RNA component of human telomerase should prevent the RNA component of human telomerase from association with the protein components, blocking the formation of active telomerase and rendering the cells mortal.

EXAMPLE 9

Identification and Isolation of RNA Component Nucleic Acids from Non-human Mammals To illustrate how the reagents of the invention can be used to identify and isolate substantially homologous nucleic acids from other mammalian species, PCR primers complementary to human RNA component sequences were used to amplify homologous sequences in a PCR. An illustrative primer pair used to demonstrate this aspect of the invention is composed of primer +10, which has the sequence 5'-CACCGGGTTGCGGAGGGAGG-3' [SEQ ID NO:24], and primer R7, which has the sequence 5'-GGAGGGGCGAACGGGCCAGCA-3' [SEQ ID NO:25]. Genomic DNA was prepared from chimpanzee, squirrel monkey, rhesus monkey, and baboon tissue and dissolved in TE buffer at a concentration of about 0.5–4 mg/ml.

For each tissue type, a PCR mixture was prepared, which mixture comprised: 1 μL of genomic DNA, 48 μL of Master Mix (Master Mix is composed of 1× TaqExtender™ buffer from Stratagene, 200 μM of each dNTP, and 0.5 μM of each primer), and 0.5 μL of a 1:1 mixture of Taq polymerase (5 Units/μL, Boehringer Mannheim): Tth polymerase (TaqExtender™ polymerase, from Stratagene). The reaction tubes were loaded onto a thermal cycler, which was programmed to first heat the reaction mixture at 94° C. for 5 minutes and then to perform 27 cycles of incubations at 94° C. for 30 sec., 63° C. for 10 sec., and 72° C. for 45 sec. After the amplification reaction was complete, about 10 μL of each reaction mixture were loaded onto a 2% agarose gel for electrophoresis. After electrophoresis, staining of the gel, and UV irradiation, one could observe that each reaction mixture contained a band of the predicted (~200 bp) size. Nucleic acids from these bands can be cloned and sequenced and the remainder of the RNA component genes from each of these mammalian species can be cloned as described above for the gene for the RNA component of human telomerase.

The foregoing examples describe various aspects of the invention and how certain nucleic acids of the invention were made. The examples are not intended to provide an exhaustive description of the many different embodiments of the invention encompassed by the following claims.

We claim:

1. A recombinant or synthetic nucleic acid comprising a promoter that comprises a nucleotide sequence that specfically hybridizes to a sequence that is identical or complementary to a sequence between nucleotides 1–1458 of SEQ ID NO:3, wherein the promoter is capable of driving transcription of a second nucleic acid.

2. The nucleic acid of claim 1, wherein the promoter comprises a nucleotide sequence identical to nucleotides 1–1458 of SEQ ID NO:3.

3. The nucleic acid of claim 1, wherein the promoter is 200 or more nucleotides in length.

4. The nucleic acid of claim 1, further comprising a second nucleic acid wherein the promoter is positioned to drive transcription of the second nucleic acid.

5. The nucleic acid of claim 4, wherein the promoter is capable of driving expression of the second nucleic acid in a cell selected from the group consisting of a mortal cell, a tumor cell, a stem cell, and a germline cell.

6. The nucleic acid of claim 4, wherein the promoter is capable of driving expression of the second nucleic acid in a tumor cell.

7. The nucleic acid of claim 4, wherein the second nucleic acid encodes an RNA component of mammalian telomerase.

8. The nucleic acid of claim 7, wherein the second nucleic acid encodes a wild-type RNA component of human telomerase or a mutant RNA component of human telomerase.

9. The nucleic acid of claim 4, wherein the second nucleic acid encodes a reporter gene.

10. An expression vector comprising the promoter of claim 1.

11. A cell comprising the expression vector of claim 10.

12. The cell of claim 11, wherein the cell is a human cell.

13. A recombinant or synthetic nucleic acid comprising a promoter, wherein the promoter comprises at least an A/T box consensus sequence and a CAAT box consensus sequence of the RNA component of human telomerase ("hTR") gene.

14. The nucleic acid of claim 13, wherein the promoter is isolated from pGRN33 (ATCC Accession No. 75926).

15. The nucleic acid of claim 13, wherein the promoter comprises at least one transcription control element of the hTR gene selected from the group consisting of a PSE consensus sequence, an SP1 consensus sequence, and a beta-interferon response element consensus sequence.

16. A method of expressing a nucleic acid in a cell, comprising the step of transforming the cell with an expression vector comprising a promoter, wherein the promoter comprises a nucleotide sequence that specifically hybridizes to a sequence between nucleotides 1–1458 of SEQ ID NO:3, wherein the promoter is capable of driving transcription of the nucleic acid and wherein the promoter is positioned to drive transcription of the nucleic acid.

17. The method of claim 16, wherein the promoter comprises a nucleotide sequence identical to nucleotides 1–1458 of SEQ ID NO:3.

18. The method of claim 16, wherein the cell is a human cell.

19. The method of claim 16, wherein the cell is selected from the group consisting of a mortal cell, a tumor cell, a stem cell, and a germline cell.

20. The method of claim 16, wherein the cell is a tumor cell.

* * * * *